United States Patent [19]
Edwards et al.

[11] 3,949,734
[45] Apr. 13, 1976

[54] FLUID PUMP CONTROL SYSTEM

[76] Inventors: Miles Lowell Edwards, 13191 Sandhurst Place, Santa Ana, Calif. 92705; Eugene G. Taatjes, 229-9th St., Huntington Beach, Calif. 92648

[22] Filed: July 22, 1974

[21] Appl. No.: 490,359

[52] U.S. Cl. ........ 128/1 D; 23/258.5 R; 128/214 F; 128/DIG. 3; 128/DIG. 12; 417/43; 417/44
[51] Int. Cl.² ......................................... A61M 1/03
[58] Field of Search......... 128/214 E, 214 F, 214 R, 128/DIG. 12, DIG. 13, DIG. 3, 1 D, 278; 23/258.5; 417/20, 43–45

[56] References Cited
UNITED STATES PATENTS

| | | | |
|---|---|---|---|
| 3,334,285 | 8/1967 | Blake | 417/45 |
| 3,465,746 | 9/1969 | Guarino | 128/1 D |
| 3,478,532 | 11/1969 | Cootey et al. | 417/44 |
| 3,572,979 | 3/1971 | Morton | 128/1 D |
| 3,756,234 | 9/1973 | Kopp | 128/214 F |
| 3,799,702 | 3/1974 | Weishaar | 128/278 |
| 3,833,013 | 9/1974 | Leonard | 128/214 R |
| 3,841,157 | 10/1974 | Willock | 128/214 E |

*Primary Examiner*—William E. Kamm
*Attorney, Agent, or Firm*—Lee R. Schermerhorn

[57] ABSTRACT

The system coordinates the speed of a blood pump, in an extracorporeal blood circuit for a patient, with the blood flow from the patient to pass the blood through a treatment device such as an oxygenator and then back to the patient. The blood from the patient flows through a bladder which actuates a transducer to control an integrator and current amplifier. The current amplifier charges a capacitor to the breakdown potential of a DIAC avalanche diode causing the diode to fire and dump the charge of the capacitor into a silicon controlled rectifier which energizes the pump motor. The speed of the motor depends on the charging time of the capacitor in response to a signal voltage from the transducer. The motor is stopped by a comparator and flip flop when the blood flow through the bladder drops to a predetermined low value. The speed of the motor may also be controlled manually by a potentiometer.

6 Claims, 2 Drawing Figures

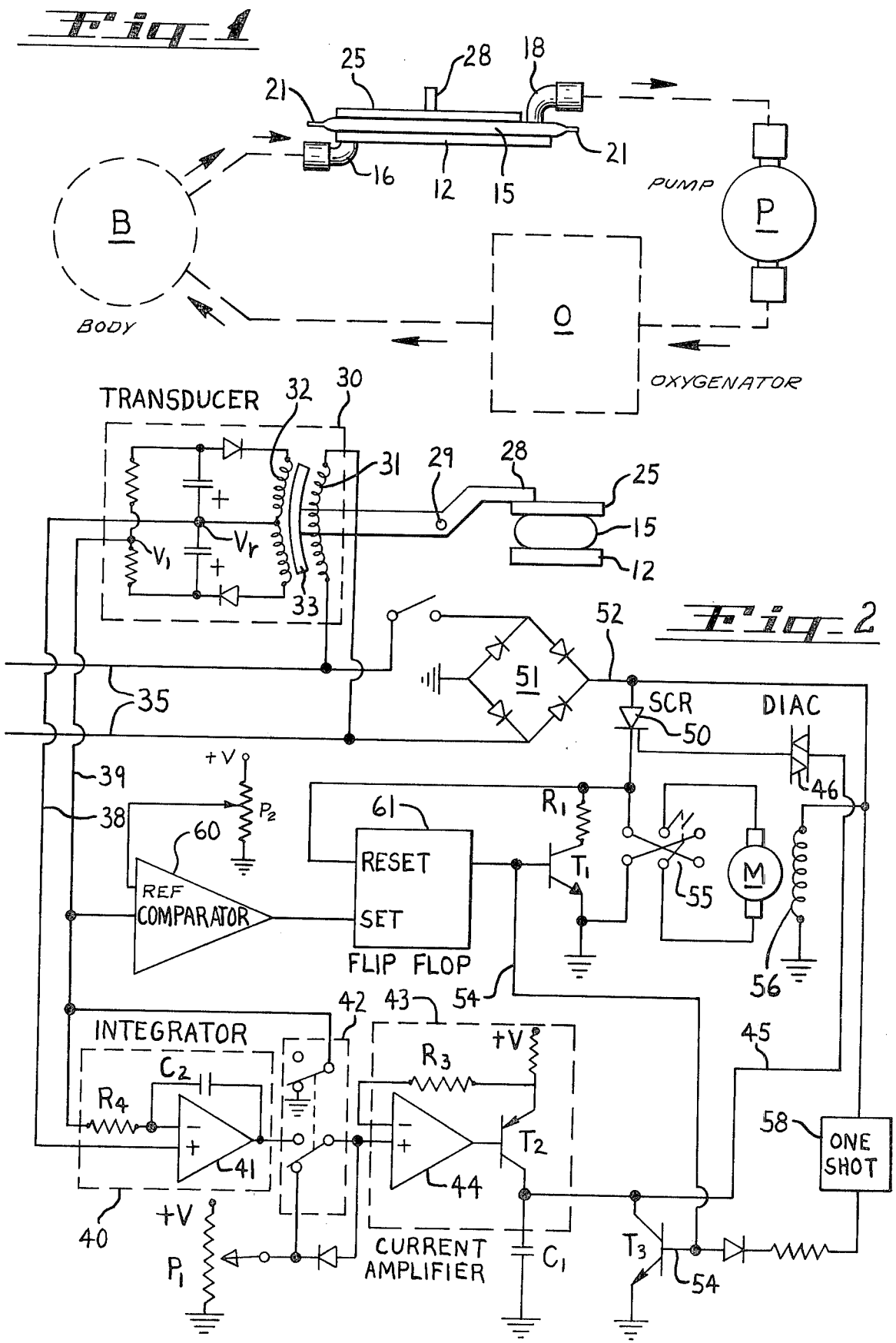

FLUID PUMP CONTROL SYSTEM

BACKGROUND OF THE INVENTION

This invention relates to a fluid pump control system for regulating the speed of a pump in accordance with the fluid supply so that the pump does not impose a back pressure on the source of supply by running too slowly and does not create suction pressure on the source of supply by running too fast. The invention is of general application for the specified purpose but it is disclosed herein with particular reference to an extracorporeal blood circuit for a patient. This invention is an improvement on the control system in the Edwards U.S. Pat. No. 3,827,828.

Open heart practices are today very well established as applied to surgical procedures where the normal blood supply to the muscles of the heart and to the brain must not be interrupted during repair of critical organs.

With the advancement of the art of fabricating membrane oxygenators, which are notably low in damage to the blood, there has been a need for developing new procedures to permit long time perfusion of a patient during periods of crisis. Patients suffering from heart attack, emphysema, asthma, or the like, may over a period of days with supplementary perfusion with well oxygenated blood develop sufficient recovery of natural organ functions to carry on without the need of the extracorporeal blood supply.

To do this it is desirable to make connection through catheterized connections to more peripheral blood vessels of the body. This avoids the necessity of opening the patient's chest for access to the larger vessels near the heart.

It is also important to provide the equipment which will permit carrying on the longer period of a procedure in an intensive care area of the hospital without usurping a surgical area for the extended period.

The present system makes it possible to operate an extracorporeal blood circuit without the close attention of a skilled pump attendant as is usually employed in cases where a short term profusion is indicated as is usual during heart syrgery.

During heart surgery, a pump and oxygenator takes over the normal functions of the heart and lungs to circulate and oxygenate the blood in order to keep those organs of the patient alive which require a continuous supply of fresh blood. An array of mechanical equipment attended by a team of specialists is necessary to do this in addition to the team of surgeons who perform the operation. One of the functions which demands constant attention is to maintain a proper speed of the blood pump so as not to let the extracorporeal circuit become too out of phase with blood supply and demands of the perfused organs. The purpose of the present device is to regulate the pump automatically so that manual supervision is not required.

Objects of the invention are, therefore, to provide an improved fluid pump control system, to provide a pump control system which regulates the speed of the pump according to the rate of flow of its source of supply, to control a pump so that it does not impose a back pressure on its source of supply by running too slowly and does not create suction pressure in its source of supply by running too fast, to provide an electric control system for the purpose described which is operable on standard 120 volt alternating current house wiring, and to provide a control system of the type described which is suitable for use in connection with the flow of blood in an extracorporeal blood circuit.

SUMMARY OF THE INVENTION

In the present pump system the speed of the pump motor is controlled by the charging rate of a capacitor in a solid state control circuit. After each charge the capacitor discharges through a silicon controlled rectifier which energizes the motor during the intervals of capacitor discharge. The capacitor can be charged faster or slower to control the speed of the motor.

The charging rate of the capacitor is controlled by a voltage which is varied by a transducer. The transducer responds to the movements of a platen bearing against a tubular bladder which conveys the fluid input to the pump. As the bladder expands, the pump is speeded up and, as the bladder contracts, the pump is slowed down. Thus, the speed of the pump is regulated to correspond to its input flow so that the pump does not impose a back pressure on the input flow by running too slowly and does not create suction pressure in the source of supply by running too fast. Under conditions of steady fluid flow in the input to the pump, the motor maintains a steady speed in equilibrium with the fluid input flow.

In addition to such normal automatic adjustments of pump speed to comply with normal small variations in the blood flow, an emergency safeguard is provided which causes the pump to stop immediately in case the blood supply is abruptly interrupted such as would occur if the blood supply tubing were suddenly closed by a kink or by an attendant stepping on it. If the blood pump were to continue to operate when the bladder is empty, the pump could draw fatal air bubbles into the blood stream. Emergency stop circuitry prevents this from happening.

The invention will be better understood and still other advantages will become apparent from the following description of the preferred embodiment illustrated on the accompanying drawing. Various changes may be made, however, in the details of construction and arrangement of the circuit and certain features may be used without others. All such modifications within the scope of the appended claims are included in the invention.

BRIEF DESCRIPTION OF THE DRAWING

FIG. 1 is a schematic diagram of the fluid circuit; and
FIG. 2 is a block diagram of the control circuit.

DESCRIPTION OF THE PREFERRED EMBODIMENT

A stationary horizontal table or shelf 12 supports a flexible tubular bladder 15. Bladder 15 conveys the blood flow from body B in an extracorporeal circuit to the pump P which is to be controlled. Pump P returns the blood to the body B through oxygenator O as indicated by the arrows.

One end of bladder 15 is provided on its underside with an inlet ell connection 16 which is received in a slot in one end of table 12. The opposite end of the bladder is provided on its upper side with an outlet ell connection 18 which is inserted in a slot in a retainer bracket (not shown) immediately above the table 12. The ell connections 16 and 18 hold the bladder in operative position on table 12 while at the same time facilitating convenient removal and replacement of the bladder. The ends of tubular bladder 15 are sealed at 21.

The tubular bladder 15 is substantially flattened and inlet and outlet ell fittings 16 and 18 have end portions sealed in the wall of the tube. These fittings have external end portions projecting in opposite directions longitudinally of the tube in offset relation thereto as shown.

A horizontal platen 25 rests on the upper side of bladder 15 and is vertically movable in response to volumetric expansion and contraction of the bladder. Platen 25 is connected to an arm 28 mounted on a horizontal pivot 29 for actuation of a transducer 30. The weight of platen 25 is sufficient to cause the platen to bear against the upper side of the bladder at all times by the force of gravity so as to rise and fall with the expansion and contraction of the bladder under varying rates of blood flow through the bladder. If the blood flow through inlet 16 should cease while the pump is running, the upper wall of the bladder immediately collapses against its lower wall, dropping the platen to an extreme lower position. In the drawing the platen is shown in an intermediate position corresponding to normal steady flow through the bladder.

Linear transducer 30 is essentially a transformer having coaxial primary and secondary coil windings 31 and 32 with an open center on an arcuate axis. These windings encircle an arcuate core 33 of magnetic material mounted on the end of arm 28 for axial movement in response to expansion and contraction of bladder 15. Primary winding 31 is energized from a 60 cycle, 120 volt alternating current supply 35, and secondary winding 32 has a center tap connected to a reference voltage terminal $V_r$. The ends of secondary 32 are connected through diodes and resistors to a signal voltage terminal $V_1$, as shown.

Under the condition of steady fluid flow through bladder 15, core 33 assumes a mid position in coils 31 and 32, producing a voltage signal at terminal $V_1$ equal to the input reference voltage at $V_r$. When bladder 15 expands from increasing fluid flow, core 33 is moved downward, producing a variable positive voltage signal at terminal $V_1$ relative to the reference voltage and when bladder 15 contracts from decreasing fluid flow, core 33 moved upward, producing a variable negative voltage signal at terminal $V_1$, relative to the reference voltage.

The transducer signal voltage at terminal $V_1$ is transmitted through wire 39 to integrator 40. Also, a wire 38 connects the reference voltage at $V_r$ to integrator 40. Integrator 40 comprises an operational amplifier 41 connected to a series resistance $R_4$ and a shunt capacitor $C_2$.

When double-pole, double-throw switch 42 is in its upper position, the signal from integrator 40 is transmitted to current amplifier 43. Current amplifier 43 comprises an operational amplifier 44 connected with a resistance $R_3$ and transistor $T_2$, as shown. This circuit requires a direct current positive voltage supply source at terminal +V.

The output of current amplifier 43 is connected through wire 45 to a DIAC avalanche 46 which controls the silicon controlled rectifier 50. Silicon controlled rectifier 50 receives the direct current power output of rectifier 51 through a wire 52.

Wire 52 is also connected to a one shot 58. The one shot output is connected to the base of transistor $T_3$ by the wire 54. The one shot short circuits the timing capacitor $C_1$ every 1/120 of a second to ground potential, thus re-starting the timing interval each 1/120 of a second.

Silicon controlled rectifier 50 energizes the armature of motor M through reversing switch 55. Motor M drives the pump P in FIG. 1. Motor M may have a permanent field magnet or a direct current field winding 56 as shown.

An emergency stop circuit is provided to stop the pump P abruptly if the fluid flow through bladder 15 should fall below a predetermined minimum. This stop circuit comprises a comparator 60 responsive to the transducer signal voltage $V_1$, a flip flop 61 receiving the comparator output, and a transistor $T_1$. The output of flip flop 61 is also connected to wire 54.

The speed of motor M is controlled by the combination of silicon controlled rectifier 50, avalanche diode 46 and capacitor $C_1$. Capacitor $C_1$ is charged positively by the current amplifier 43 to the breakdown potential of avalanche diode 46 at which time the avalanche diode fires and dumps the charge of capacitor $C_1$ into the silicon controlled rectifier 50, allowing the silicon controlled rectifier to delivery deliver pulse of energy to the motor. By controlling the voltage to the current amplifier 43, the capacitor $C_1$ can be charged repetitively faster or slower to vary the speed of the motor. With switch 42 in the upper position for automatic operation, the current amplifier 43 is controlled by integrator 40 from the signal voltage at $V_1$ in linear transducer 30.

Changes in blood flow through bladder 15 produce a proportional change in the voltage level at terminal $V_1$. The transducer 30 is adjusted to provide an output voltage at $V_1$ equal to reference voltage $V_r$ when the blood flow is steady. An increase in blood flow produces a variable positive voltage at $V_1$ and a reduced blood flow produces a variable negative voltage at $V_1$. In response to these signals, the integrator 40 and current amplifier 43 speed up or slow down motor M until equilibrium is again established within an operating range.

Comparator 60, flip flop 61 and transistor $T_1$ provide an emergency stop circuit. If the blood flow through bladder 15 decreases below a predetermined level, the comparator sets the flip flop. The flip flop turns off the current amplifier 43 by means of transistor $T_3$, causing the armature windings to be short-circuited through resistance $R_1$ and transistor $T_1$. This produces the effect of a magnetic brake to stop the motor quickly. When the voltage across the motor armature windings reaches zero, the flip flop is automatically reset, causing the motor to resume normal operation as soon as the voltage at transistor terminal $V_1$ signals resumption of the blood flow.

Comparator 60 includes within its internal circuitry a preset reference input which is adjusted only during the initial setup of the pump. This is represented by positive direct current source +V and potentiometer $P_2$.

The flip flop 61 is set and reset by a zero voltage. The set and reset inputs are normally held at a positive voltage; a momentary zero voltage sets or resets the flip flop. The reset input is connected across motor M; therefore, in the running mode, the reset input has some voltage on it. When the motor is not running, the reset input is at zero voltage, thus turning off the flip flop and transistor $T_1$ to make sure it is not in an emergency stop condition when the motor starts again.

The energizing circuit for the armature of motor M is turned off when flip flop 61 is set, a signal through wire 54 turning on transistor $T_3$ and transistor $T_3$ turning off silicon controlled rectifier 50. Transistor $T_1$ then short circuits the motor armature through resistance $R_1$.

Provision is also made for manual control of the motor speed. When switch 42 is placed in the lower or manual position as shown, the charging rate of capacitor $C_1$, and hence the speed of the motor, is controlled by the speed adjusting potentiometer $P_1$. Potentiometer $P_1$ is supplied by separate positive direct current source +V.

Reversing switch 55 is used to reverse the fluid flow for cleaning the fluid circuit after use with blood.

Having now described our invention and in what manner the same may be used, what we claim as new and desire to protect by Letters Patent is:

1. In an extracorporeal blood circuit for a patient, a pump driven by a variable speed electric motor, and a control system for said motor to regulate the speed of said pump so that the pump does not impose a back pressure on the input flow from the patient by running too slowly and does not create suction pressure on the input flow from the patient by running too fast; said control system comprising a flexible bladder connected in said inlet flow from the patient so as to expand and contract in accordance with the rate of said inlet flow of blood from the patient relative to the output of the pump, a platen bearing on said bladder and movable with the expansion and contraction of the bladder, circuit means operable by said platen to increase the speed of said motor in accordance with the amount of movement of the platen in one direction when the bladder is expanding and operable to decrease the speed of said motor in accordance with the amount of movement of the platen in an opposite direction when the bladder is contracting; and circuit means operable by said platen to stop said motor in response to excessive contraction or substantial collapse of the bladder; said first circuit means comprising a silicon controlled rectifier in circuit with said motor, a capacitor, a transducer connected with said platen and having circuit means arranged to vary the charging time of said capacitor, and means for discharging said capacitor through said rectifier to energize said motor, the frequency of discharge of said capacitor controlling the speed of said motor; said circuit means arranged to vary the charging time of said capacitor comprising an integrator and current amplifier connected in series between said transducer and capacitor, said means for discharging said capacitor comprising an avalanche diode; said transducer comprising coaxial primary and secondary coils, said primary coil being connected across an AC supply, a center tap in said secondary coil connected to a reference voltage terminal, a core of magnetic material movable axially in said coils by said platen, a pair of resistors each connected at one end to a signal voltage terminal, a pair of diodes connected between the ends of said secondary coil and the other ends of said resistors, respectively, and a pair of condensers connected between said reference voltage terminal and said other ends of said resistors, respectively.

2. A system as defined in claim 1, said bladder comprising a tube having inlet and outlet connections in its opposite ends.

3. A system as defined in claim 1, said bladder comprising a substantially flattened tube, seal lines closing opposite ends of said tube, and inlet and outlet ell fittings having end portions sealed in the wall of said tube in opposite sides thereof at opposite ends thereof, said fittings having external end portions projecting in opposite directions longitudinally of the tube in offset relation thereto.

4. A system as defined in claim 1, said signal voltage terminal and reference voltage terminal providing the input to said integrator.

5. In an extracorporeal blood circuit for a patient, a pump driven by a variable speed electric motor, and a control system for said motor to regulate the speed of said pump so that the pump does not impose a back pressure on the input flow from the patient by running too slowly and does not create suction pressure on the input flow from the patient by running too fast; said control system comprising a flexible bladder connected in said inlet flow from the patient so as to expand and contract in accordance with the rate of said inlet flow of blood from the patient relative to the output of the pump, a platen bearing on said bladder and movable with the expansion and contraction of the bladder, circuit means operable by said platen to increase the speed of said motor in accordance with the amount of movement of the platen in one direction when the bladder is expanding and operable to decrease the speed of said motor in accordance with the amount of movement of the platen in an opposite direction when the bladder is contracting; and circuit means operable by said platen to stop said motor in response to excessive contraction or substantial collapse of the bladder; said first circuit means comprising a silicon controlled rectifier in the energizing circuit for the armature of said motor, a capacitor, a transducer connected with said platen and having circuit means arranged to vary the charging time of said capacitor, and means for discharging said capacitor through said rectifier to energize said motor, the frequency of discharge of said capacitor controlling the speed of said motor; said circuit means arranged to vary the charging time of said capacitor comprising an integrator and current amplifier connected in series between said transducer and capacitor, said means for discharging said capacitor comprising an avalanche diode; said circuit means operable by said platen to stop said motor comprising a comparator and flip flop controlled by said transducer to turn off said current amplifier, a transistor connected to the output of said current amplifier, said transistor being turned on by said flip flop and said transistor then turning off said silicon controlled rectifier to open the energizing circuit to the armature of said motor in the event of excessive contraction or substantial collapse of the bladder, and a transistor connected across said armature and turned on in said event by said flip flop to short circuit said armature.

6. A system as defined in claim 5, said integrator receiving a signal output from said transducer and said current amplifier receiving the output from said integrator, a manual potentiometer speed control for said motor, and a switch between said integrator and current amplifier arranged to switch the input to said current amplifier from said integrator to said potentiometer.

* * * * *